United States Patent

Rogala

[11] Patent Number: 5,911,759
[45] Date of Patent: Jun. 15, 1999

[54] ACETABULUM ENDOPROSTHESIS AND HEAD

[76] Inventor: Piotr Rogala, Podolska 6, PL-60-615 Poznan, Poland

[21] Appl. No.: 08/809,117

[22] PCT Filed: Sep. 14, 1995

[86] PCT No.: PCT/PL95/00020

§ 371 Date: May 14, 1997

§ 102(e) Date: May 14, 1997

[87] PCT Pub. No.: WO96/08214

PCT Pub. Date: Mar. 21, 1996

[30] Foreign Application Priority Data

Sep. 16, 1994 [PL] Poland ..................... 305060

[51] Int. Cl.⁶ .......................... A61F 2/32
[52] U.S. Cl. .................. 623/22; 623/19; 623/18
[58] Field of Search .............. 623/22, 23, 20, 623/19, 18, 16

[56] References Cited

U.S. PATENT DOCUMENTS

| | | |
|---|---|---|
| 2,910,978 | 11/1959 | Urist . |
| 3,840,904 | 10/1974 | Tronzo . |
| 4,659,331 | 4/1987 | Matthews et al. ............ 623/22 |
| 4,919,677 | 4/1990 | Stuhmer et al. ............ 623/22 |
| 5,108,448 | 4/1992 | Gautier ........................ 623/22 |
| 5,358,532 | 10/1994 | Evans et al. ................ 623/22 |
| 5,609,646 | 3/1997 | Field et al. ................. 623/22 |

FOREIGN PATENT DOCUMENTS

| | | |
|---|---|---|
| 009 148 | 4/1980 | European Pat. Off. . |
| 013 863 | 8/1980 | European Pat. Off. . |
| 2 598 908 | 5/1986 | France . |
| 2 519 545 | 1/1992 | France . |
| 2 686 503 | 1/1992 | France . |
| 2 150 441 | 7/1985 | United Kingdom . |

*Primary Examiner*—Michael J. Milano
*Assistant Examiner*—Tram A. Nguyen
*Attorney, Agent, or Firm*—Burns, Doane, Swecker & Mathis, L.L.P.

[57] ABSTRACT

An implantation method is described which involves the successive introduction of projecting multilateral needles into the spongy bone of a joint. The needles are symmetrically spaced on the terminal surfaces of the endoprosthesis up to a resistance edge on one portion of an endoprosthesis and up to a resistance surface on a second portion of the endoprosthesis. The remaining free area between the projecting multilateral needles is filled up to the terminal surfaces in the "biological silence" by osteoblasts. The endoprosthesis also includes a glenoid cavity and a head which have round terminal surfaces with the projecting multilateral needles placed thereon. The projecting multilateral needles have different lengths and mutually parallel axes which are perpendicular to the planes in which the round resistance edge of the glenoid cavity and the resistance plane of the head are located.

20 Claims, 1 Drawing Sheet

ACETABULUM ENDOPROSTHESIS AND HEAD

BACKGROUND OF THE INVENTION

1. Field of the Invention

The present invention relates to an endoprosthesis to apply in bone surgery, without using surgical cement, and more particularly to a prosthetic acetabulum and head.

2. Brief Description of the Related Art

There are known endoprosthesis the connection of which with the bone takes place by the growing into pores of proper dimensions, into indentations and other irregularities on the surface of the endoprosthesis, fixed on the spot where it is mounted with the help of surgical cement, or mechanically. In order to stop bone loss, it has been proposed to use an endoprosthesis joined with the bone by pushing surgical cement into the marrow cavity for example, polymethylmethacrylate cement, or with the help of coarse threads. These endoprostheses suffer from a very small bonding surface formed by ingrowth of spongy bone.

Furthermore, the joining of an endoprosthesis to the bone by surgical cement has some defects. The main defect is that the material weakens as it ages, which causes it to fail. Consequently, irritation from the failing cement causes a separation from the bone and this, in turn, causes loosening of the endoprosthesis and the bone's atrophy.

DE 3443109 A1 describes a prosthesis in which the prosthetic implants have more secure fastenings by applying conic irregularities which stick out of the terminal surface of the endoprosthesis and which are directed against the 'joining surface of the bone. The conic irregularities are pressed into the spongy bone and cause an increase in the contact surface which is favourable to fixation of the prosthesis to the bone by bone ingrowth. An imperfection of this solution is the fact that there is no possibility to optimally increase the contact surface of the endoprosthesis with the bone because the conic irregularities are spaced apart on a plane surface. However, the plane contact surface, because of it's shape, renders impossible ingrowth of spongy bone in a shape similar to the natural form, which would assure a good absorption of the joint's forces.

FR A 2 519 545 describes a prosthesis in which the acetabulum has a total spherical form and also, on the top of the endoprosthesis, includes conic irregularities which stick out of the boundary surface of the endoprosthesis and which are directed against the joining surface of the pelvic bone; this structure, however, is not adapted to the physiological structure of the bone. For this reason it can not be implanted due to the fact that the "bottom" of the acetabulum in the bone of the pelvis is flat, hard and made out of a thin cortex in the pelvic bone. Therefore, the needle on the top of the acetabulum cap can cause a perforation of the bone, which causes a weakening and finally a damage thereto: a bleeding of the blood vessels inside the pelvis.

Another deficiency of the device described in FR A 2 519 545 is the insertion of the endoprosthesis, which occurs at the same time as implantation of the needles in the cap. Furthermore, insertion of the endoprosthesis in such a form, in which all of the needles have the same length and extend over the highest point of the external surface of the acetabulum, is imperfect because of the anatomical structure of the pelvis bone. Such an installation of the endoprosthesis makes impossible bone ingrowth between the sharply ended needles, and therefore causes a weak connection of the bone with the endoprosthesis, because the connection is purely mechanical and causes unfavourable transmission of the biomechanical forces of the hip joints.

FR A 2 686 503 describes a prosthesis in which the endoprosthesis facilitates only a partial reconstruction of the femoral head surface, which has been removed because of necrosis. The imperfection of this invention is that the endoprosthesis does not permit resection of the whole femoral head surface. Additionally, implantation of the endoprosthesis requires a special hole for the keel 5, which complicates the surgery and diminished the adhesion. Because the endoprosthesis according to this solution diminished the adhesive interface surface, it is not stable for a non-cemented solution.

SUMMARY OF THE INVENTION

The aim of the invention is the elimination of these imperfections by creating an endoprosthesis, thanks to which there is a simple, safe and durable union with the bone tissue of the cortex as well as the trabecular bone, ensuring at the same time the possibility of rebuilding the regenerated bone in a form similar to the natural and original bone.

This aim has been achieved thanks to this invention according to which an endoprosthesis includes an acetabulum and a head, while the bearing surfaces are located on round surfaces which include multilateral projecting needles, preferably in the form of a pyramid with parallel axes and different lengths. The edges of the bases of adjacent needles contact each other, and their axes are substantially perpendicular to the surface in which lies the bearing edge of the acetabulum as well as the bearing surface of the head. The total interface bearing surfaces are advantageously more than seven times larger than the joint surface of the acetabulum and the head, and the needles advantageously are sized so that the ratio of the half diagonal to the height of the pyramid is more than one to five. Peaks of the projecting multilateral pyramid needles of the acetabular cap do not extend beyond the circular boundary surface determines by the edge lying on the plane perpendicular to the acetabular axis, however the head has a bearing surface in annular form with an outer diameter less than a diameter of the round bowl which constitutes a spherical cap of the external surface of the head.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which.

DESCRIPTION OF THE PREFERRED EMBODIMENTS

Figure 1:
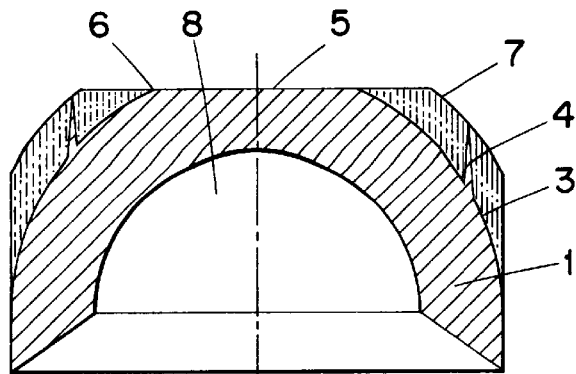
FIG. 1 schematically illustrates the acetabulum of the endoprosthesis in cross-section.
Figure 2:
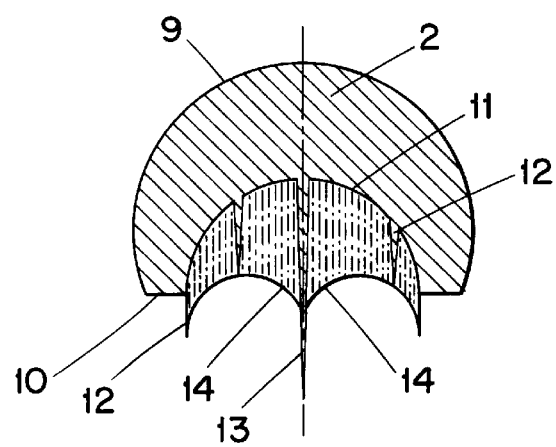
FIG. 2 schematically illustrates the head of the endoprosthesis in cross-section.
Figure 3:
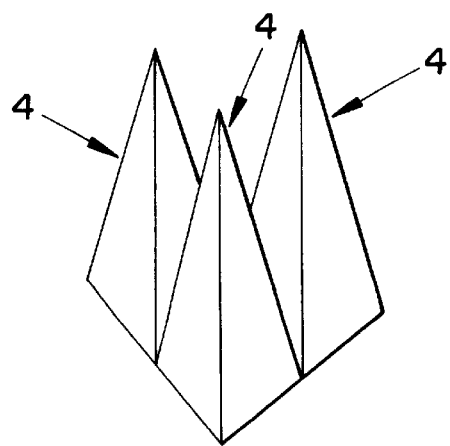

Referring to the drawing figures, like reference numerals designate identical or corresponding elements throughout the several figures.

The endoprosthesis of the joints is composed by the acetabulum (1) and the head (2). The acetabulum (1) has an external spherical boundary surface (3) which is equipped with multilateral needles (4). A circular surface (5) is determined by the edge (6) lying in the perpendicular plane to the longitudinal axis of the acetabulum. The multilateral needles (4) are preferably of pyramid form (not shown in the figures) which have common edges with the bases of neighbouring needles (4) and have differing lengths. The length of the multilateral needles (4) measured from the base on the boundary surface (3) determines a concentric line to the boundary surface (3), the theoretical spherical surface (7) which crosses the peaks of a part of the multilateral needles (4) as well as the plane in which lies the circular surface (5), so the peaks of the multilateral needles (4) do not exceed the plane in which lies the edge (6), whilst the ratio of the half diagonal of the needle bases to the height of the needle pyramid is at least one to five, and the total surface area of the multilateral needles (4) is more than at least seven times more than that of surface (9).

The acetabulum (1) is equipped with a pan (8) to place the head (2) which constitutes a part of the spherical cap of the external surface (9). The head (2) has a annular bearing surface (10) lying below the transverse axis of the head (2) in a perpendicular plane to the concentric line, and a spherical boundary surface (11). Boundary surface (11) defines a spherical cap, designated by a ray which equals a half of the diameter from the two inner edges of the bearing surface (10), beginning from the bisection point of the concentric axis of the head (2) in which the bearing surface (10) is located. On the spherical boundary surface (11) there are multilateral needles (12) and a central multilateral needle (13) with parallel axes to each other, and the multilateral central needle is coincident with the axis of the head (2). The multilateral needles (12) have common edges at their bases (not shown in figures) with neighbouring multilateral needles (12), and have differing lengths. The tip of the central multilateral needle (13) lies on the sphere which includes the surface (9). The remaining lengths of the multilateral needles (12) are determined by the distance between their base on the boundary surface (11) to the tips which lie on the theoretical surface of the caps (14) with a radius which is equal to the half of the distance between the axis of the multilateral needles (12) and the axis of the multilateral central needle (13) carried out from the point which lies between the axes on the straight line which connects the peaks of opposite extreme needles (12), so that the remaining needles are longer than the multilateral ones (12).

The ratio of the half diagonal of the base of the multilateral needles (12) and (13) to the height of the pyramid is at least one to five. The surfaces of the multilateral needles (12) and the surfaces of the multilateral central needle (13) have a total surface more than seven times bigger than that of the surface (9). This reflects approximately the internal surface of the essence of the bone bark on which the head is implanted. Another such advantageous surface constitutes the joint surface of the multilateral needles (4). The different lengths and placed multilateral needles (4) and (12) causes their steady, easy and successive introduction into the spongy bone to a depth determined by contact with the bone of the edge (6) and the bearing surface (10).

Insertion of the endoprosthesis of the present invention is simultaneously performed along the axis of the bone's head. The central needle (13) of the endoprosthesis's head (2) is introduced into the spongy bone until the bearing surface (10) contacts the cortex and the adjacent spongy trabecular structure, into which are simultaneously introduced multilateral needles (12). Needles (12) are introduced into that part of the bone which is at a distance larger than that of the plane of the bearing surface (10), and the space between the remaining needle (12) which have not been introduced into the spongy bone until the bearing surface (11) is filled up 'in "biological silence" by osteoblasts.

The glenoid cavity of the endoprosthesis is implanted according to the method of this invention so that the edge (6) is brought into contact with the bone, and is positioned on the bone perpendicular to the central axis of the acetabulum of the bone. The edge (6) is placed symmetrically with regard to the axis. The needles which are near the spherical belt on the boundary surface of the endoprosthesis are simultaneously partially introduced into the spongy structure of the bone. The remaining surface between the multilateral needles (4) which are not introduced into the spongy bone down to the boundary surface (3) are filled by osteoblasts in "biological silence".

The bearing edge (6) as well as the bearing surface (10) properly bear on the bone of the pelvis acetabulum and on the bark edge of the bone tight femoral neck. The needles' proportions, according to present invention, considerably increases the adhesion when bearing on the spongy bone, which causes a more effective absorption of forces, and moreover increases the fixation power in the bone tissue, thus preventing the endoprosthesis from spraining and loosening.

After new bone formation, the boundary surface (3) of the acetabulum (1), the boundary surface (11) of the head (2), surface (5), bearing surface (10) and the surfaces of the multilateral needles (4), (12), and (13) become the bearing surfaces of the endoprosthesis.

The endoprosthesis is produced in various dimensions properly fixed according to the gradation of biological sizes, and from biologically non-toxic materials, and is possessing the proper mechanical properties. The acetabulum as wen as the head can be produced entirely out of plastics with a varying density gradation so that its resistance power would be a function of the varying spring energy of the plastic, decreasing in due measure, as it removes from the surface in both parts of the endoprosthesis which achieves a suppression of the power activities which occur in the joint's system.

One of the advantages of the endoprosthesis is the proper arrangement of power between the bone and the endoprosthesis. Moreover, the implantation operation is simplified and can be performed with sick people in a considerably wider age range.

Another advantage is the longer durability of the endoprosthesis and, if necessary, it is easy to replace because the endoprosthesis in its shape is always very close to the biological model. At the same time, the endoprosthesis facilitates its application with patients with severe osteoporosis and enables implantation without using surgical cement.

Also it should be emphasized that endoprosthesis implantation according to this invention causes less injuries to the bone tissues.

The endoprosthesis in biologically verified dimensions according to this invention can be applied in operations of bone surgery on all spherical joints which occur with people and in animals and especially with implantations of hip joints, elbow joints, knee joints, shoulder joints, ankle bone joints, hand and foot joints as well as with implantations of inter-vertebra discs. The subject of this invention can be applied also in all other cases of similar biomechanical properties. While the invention has been described in detail with reference to preferred embodiments thereof, it will be apparent to one skilled in the art that various changes can be made, and equivalents employed, without departing from the scope of the invention.

I claim:

1. An endoprosthesis for implantation in a joint, comprising:

an acetabulum prosthesis comprising a cap having an exterior surface and an interior surface, a plurality of substantially parallel cap needles extending from said cap exterior surface, and a cap axis; and a prosthetic head comprising an exterior surface sized to fit within said cap interior surface, an interior surface, a plurality of substantially parallel head needles extending from said head interior surface, and a head axis;

wherein a total surface area of at least one of all of said cap needles and all of said head needles is at least seven times greater than a total surface area of said head exterior surface.

2. The joint endoprosthesis according to claim 1, wherein said cap exterior surface is substantially hemispherical, said head exterior surface is shaped as a portion of a sphere, and said head interior surface is substantially hemispherical.

3. The joint endoprosthesis according to claim 1, wherein each of said cap needles is multilateral.

4. The joint endoprosthesis according to claim 3, wherein each of said cap needles is pyramidal.

5. The joint endoprosthesis according to claim 1, wherein each of said cap needles comprises a base, and the bases of adjacent cap needles contact each other.

6. The joint endoprosthesis according to claim 1, wherein the ratio of one-half of the largest cross-sectional dimension to the height of each said cap needle is at least 1:5.

7. The joint endoprosthesis according to claim 1, wherein said cap exterior surface comprises a central planar bearing surface substantially perpendicular to said cap axis.

8. The joint endoprosthesis according to claim 7, wherein said cap needles comprise needles immediately adjacent said cap central planar bearing surface shorter than said cap needles.

9. The joint endoprosthesis according to claim 1, wherein a total surface area of all of said cap needles is at least seven times greater than a total surface area of said head exterior surface.

10. The joint endoprosthesis according to claim 1, wherein said cap needles each comprise a needle length and a needle end, said cap needle lengths being selected such that said cap needle ends are all located on one side of a plane coincident with said cap bearing surface.

11. The joint endoprosthesis according to claim 1, wherein each of said head needles is multilateral.

12. The joint endoprosthesis according to claim 11, wherein each of said head needles in pyramidal.

13. The joint endoprosthesis according to claim 1, wherein each of said head needles comprises a base, and the bases of adjacent head needles contact each other.

14. The joint endoprosthesis according to claim 1, wherein the ratio of one-half of the largest cross-sectional dimension to the height of each said head needle is at least 1:5.

15. The joint endoprosthesis according to claim 1, wherein said head exterior surface comprises a peripheral planar bearing surface substantially perpendicular to said head axis.

16. The joint endoprosthesis according to claim 5, wherein said head needles comprise needles immediately adjacent said head peripheral planar bearing surface shorter than said head needles.

17. The joint endoprosthesis according to claim 1, wherein said head needles comprise a central needle extending from said head interior surface which is longer than the remaining head needles.

18. The joint endoprosthesis according to claim 1, wherein a total surface area of all of said head needles is at least seven times greater than a total surface area of said head exterior surface.

19. The joint endoprosthesis according to claim 1, wherein said head bearing surface is substantially annular, including an external diameter less than a diameter of said head exterior surface.

20. The joint endoprosthesis according to claim 1, wherein a total surface area of said cap needles and a total surface area of said head needles are both at least seven times greater than a total surface area of said head exterior surface.

* * * * *